United States Patent [19]

Biesalski

[11] Patent Number: 5,112,598

[45] Date of Patent: May 12, 1992

[54] VITAMIN A AEROSOL-INHALATE PREPARATIONS

[75] Inventor: Hans K. Biesalski, Albig, Fed. Rep. of Germany

[73] Assignee: Hermes Fabrik Pharmazeutischer Preparate Franz Gradinger GmbH & Co. KG, Grosshesselohe, Fed. Rep. of Germany

[21] Appl. No.: 346,439

[22] Filed: May 2, 1989

[30] Foreign Application Priority Data

May 4, 1988 [DE] Fed. Rep. of Germany ....... 3815221

[51] Int. Cl.$^5$ .......................... A61L 9/04; A61L 9/14; A61L 31/07; A01N 31/04
[52] U.S. Cl. .................................. 424/46; 424/45; 514/725
[58] Field of Search ............................ 424/45, 46, 78; 514/725

[56] References Cited

U.S. PATENT DOCUMENTS

| | | | |
|---|---|---|---|
| 4,124,707 | 11/1978 | Green et al. | 514/75 |
| 4,241,048 | 12/1980 | Durbak et al. | 424/45 |
| 4,267,173 | 5/1981 | Draper | 514/887 |
| 4,614,747 | 9/1986 | Loeu et al. | 514/529 |
| 4,826,871 | 5/1989 | Gressel et al. | 514/461 |

Primary Examiner—Thurman K. Page
Assistant Examiner—Carlos Azpuru
Attorney, Agent, or Firm—Townsend and Townsend

[57] ABSTRACT

A pharmaceutical preparation consisting of retinoic acid and/or an ester of retinoic acid and/or an ester of retinol as active substances, which are present in the preparation form of an aerosol, is advantageously suitable for topical treatment of mucosal diseases in man and animal.

30 Claims, 3 Drawing Sheets

VITAMIN A AEROSOL-INHALATE PREPARATIONS

The invention relates to a pharmaceutical preparation.

BACKGROUND OF THE INVENTION

The term Vitamin A stands for a number of chemically similar compounds with different effect in the human and animal organism. These include as essential groups the alcohol of the vitamin, retinol, the transport form of the vitamin in blood, the aldehyde, the biologically active metabolite in the visual process, retinyl ester, the storage form of the vitamin in the liver and in mucous membranes and reproductive glands, and retinoic acid with various derivatives which play a part in particular in the differentiation processes of the skin. The vitamin is essential to man, i.e. a vitamin deficiency results if it is not taken in with food. The vitamin A deficiency manifests itself, depending on the duration of deprivation in hornification of the mucous membranes (Biesalski, H. K. Stofft, E., Wellner U., Niederauer, U., and Bässler, K. H. Vitamin A and ciliated cells. I. Respiratory epithelia, "Z. F. Ernährungswissenschaft: 25, 114-122 (1986), and McDowell E. M., Keenan K. P., Huang M.: Effect of Vitamin A deprivation on Hamster, Brachial Epithelium, Virchow's Arch. (Cell. Pathol.), 45:197-219, 1984 and McDowell E. M., Keenan K. P., Huang M.; Restoration of mucociliary Brachial Epithelium following Deprivation of Vitamin A, Virchow's Arch. (Cell. Pathol.) 45:221-240, 184), in particular of the respiratory system, increased susceptibility to infections and with pronounced defect in the classic symptoms of keratinization of the conjunctiva of the eye up to complete destruction and blindness.

On intake of the vitamin most of the deficiency-enhanced alterations are reversible, in particular in the area of the mucous membranes. These typical changes induced by the vitamin A deficiency are found in similar manner in diseases of the mucous membranes of the respiratory system as caused by acute and chronic bronchitis, nicotine inhalation and also early cancerous changes. It has been possible to show in experimental investigations on animals and on humans that such changes not induced by vitamin A deficiency could be made reversible by systemic intake of the vitamin, usually in high doses. In particular in various forms of cancer the use of large-dose systemic vitamin A therapy is described with varying success in the sense of preventing recidivation after primary treatment of the tumor.

In systemic administration, to obtain a regression of the squamous metaplasia or to prevent renewed occurrence of such changes high concentrations must be used which in some cases lead to substantial side effects (cerebral pressure symptoms, liver cell metabolism disturbances, and others). In addition, there is a pronounced teratogenic effect in the first three-month period which forbids use of large-dose therapy in pregnancy (Bauernfeind JC. (1980): The safe use of vitamin A, The nutrition foundation, Washington DC).

Furthermore, an intake of vitamin A is also inadmissible in physiological concentration in the presence of disturbances of liver cell metabolism such as inflammation or cirrhosis because due to the simultaneously disturbed protein synthesis (lack of formation of the transport protein - RBP=retinol-binding protein) of the liver removal of the vitamin from the stores into which it is transferred after absorption is not possible and consequently further damage to the liver would arise (Smith, F. R. and Goodman, D. S. The effect of diseases of the liver, thyroid, and kidneys on the transport of vitamin A in human plasma. J. Clin. Invest.: 50, 2426 (1971); Weber, F. L., Mitchell, G. E., Powell, D. B., Reiser, B. J. and Banwell, J. G. Reversible hepatoxicity associated with hepatic vitamin A accumulation in a protein deficient patient. Gastroenterology: 82, 118-123 (1982). In addition, the vitamin can only be taken up by the peripheral target tissue, such as the respiratory epithelium, and carry out its function when it is bound to precisely this transport protein.

An object of the present invention is therefore to avoid these disadvantages, in particular to permit an action of the vitamin A or similar compounds on the mucous membranes of the urogenital tract, intestinal tract and the respiratory epithelium, the epithelia of the nose-throat cavity and preferably the epithelia of the tracheal and deep bronchial tract.

SUMMARY OF THE INVENTION

This problem is solved according to the invention by a pharmaceutical preparation which consists of retinoic acid and/or an ester of retinoic acid and/or an ester of retinol as active substances, which are present in the preparation form of an aerosol. This permits in particular a topical action of the active substance on the mucous membranes.

In particular, according to the invention esters of retinol with physiologically compatible carboxylic acids and esters of retinoic acid with alcohols can be advantageously employed.

DETAILED DESCRIPTION OF THE INVENTION

Figure 1:
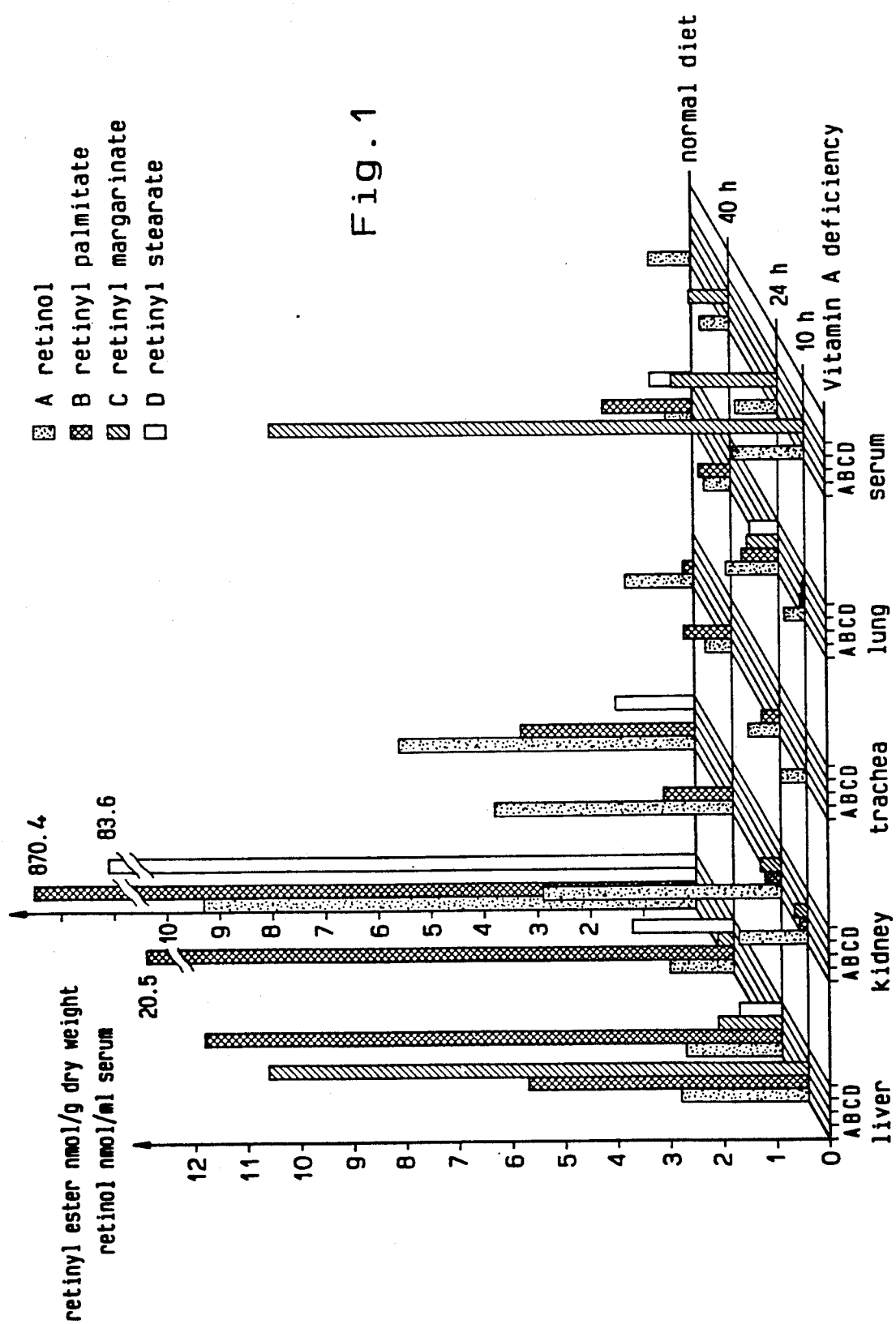
FIG. 1 is a plot showing the distribution of retinol and retinyl esters in the body at various times after parenteral administration of retinyl margarinate.

Particularly advantageous as carboxylic acids for preparing the retinol esters according to the invention are the saturated and unsaturated fatty acids, in particular the endogenously occurring fatty acids.

Of quite particular advantage are palmitic acid and/or stearic acid and/or oleic acid and/or linoleic acid and/or linolenic acid.

Particularly advantageous alcohols to be used according to the invention for preparing the retinoic acid esters are monovalent and/or multivalent primary and/or secondary and/or tertiary aliphatic and/or alicyclic and/or aromatic alcohols.

Very particularly advantageous are the aliphatic, monovalent primary alcohols, in particular methanol and ethanol and the fatty alcohols.

Sprays and inhalates, in particular deep-action inhalates, can in particular be used as aerosols according to the invention.

According to the invention it is achieved that the active substance is converted to an aerosol so that the finely distributed minute active substance particles of the aerosol reach the place of action, for example the mucous membrane of the respiratory system.

According to the invention aerosols or sprays means disperse systems of gases with solid of liquid particles distributed therein of about $10^{-7}$ to $10^{-1}$ cm diameter. Consequently, with regard to the pharmaceutical preparation according to the invention the following distinctions are to be made:

A) distributions of solid active substance particles in the carrier gas (dust aerosols) and B) distributions of active-substance-containing liquid in the carrier gas (mist aerosols).

The socalled mist aerosols can in turn be present as a) distribution of the active substance disolved in a non-aqueous lipophilic readily volatile and physiologically compatible solvent in the carrier gas or as b) distribution of a solution or dispersion of the active substance or an emulsion of the active substance present in liquid form in water or mixtures of water and or water-miscible physiologically compatible liquids in the carrier gas.

Among others, the following known technological systems are possible for the technical execution of preparations which serve for administration of an active substance according to the invention in the form of a spray or aerosol distribution:

1. Pump atomizer:

By means of a piston pump mechanism in the spray head an excess pressure is generated in the atomizer vessel containing the active substance solution or dispersion and as a result the active-substance-containing liquid is forced through the atomizer jet and thus distributed in the surrounding air (advantageously suitable for aerosols of the type Bb).

2. Aerosol propellent gas packs:

A propellent gas ensures the excess pressure in the container from which by opening the closure valve the suspended or dissolved active substance is forced through the atomizer jet and distributed. A distinction is made between:

a) Liquid gas systems:

A liquefied gas is used as propellent gas (e.g. low-boiling FCHC or propane, butane), the system being designed as aa) two-phase aerosol: here the propellent gas in the pressure container is in the liquid and gaseous phase, the liquid phase simultaneously containing dissolved the active substance and any auxiliary substances, such as additional solvents (advantageously suitable for aerosols of type Ba).

ab) suspension aerosol: the active substance particles are suspended in solid form in the liquid propellent phase (advantageously suitable for aerosols of type A).

ac) three-phase aerosol: in addition to the gaseous and liquid propellent phase there is a liquid phase of the active substance solution not miscible with the propellent. In contrast to 2aa) and 2ab) in the spraying operation as long as the package still contains active substance phase no propellent is ejected, the latter serving in this case solely to generate the operating pressure in the package (advantageously suitable for aerosols of type B).

b) pressurized gas system: in this case instead of the liquefied gas a compressed gas (e.g. nitrogen, carbon dioxide, dinitrogen monoxide, air) is used. When the valve is opened the active substance phase is forced via the rise tube dipping thereinto through the atomizer valve. The propellent gas reaches the outside only to the extent in which it is soluble in the active substance phase; when using a two-chamber pressurized pack however this is not the case at all because the active substance phase is disposed in a separate plastic bag in the pressurized can and is not in direct contact with the propellent gas (advantageously suitable for aerosol of type B).

Thus, according to the invention the pharmaceutical preparation according to the invention is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

According to the invention the carrier gas may be part of the pharmaceutical preparation in the form of a propellent gas or a solvent vaporizing on atomization, as in the case of the aerosol propellent gas package. The carrier gas may also however be atmospheric air which for atomizing the active-substance-containing liquid is conducted for example as strong air stream over the opening of a capillary tube which dips into the liquid and through which the solution is sucked up and then dispersed in the carrier gas stream. Said carrier gas stream may for example be generated by a compressor integrated into the atomizer apparatus. Finally, the stationary ambient air may also be used as carrier gas, in which the fine droplets of the active-substance-containing liquid are dispersed after they have been generated for example in the atomized jet of a pump spray, three-phase aerosol or a two-chamber pressure pack.

Another possibility for the atomization is a mechanical dispersion of the liquid containing the active substance or the active substances, for example by ultrasonic waves for example with the aid of a commercially available ultrasonic inhalator.

The active substance or the active substance combination is preferably used in stabilized form; this is achieved for example by addition of butyl-hydroxyanisole (BHA) and/or butylated hydroxytoluene (BHT) or gamma-tocopherol or alpha-tocopherol or tocopherol mixtures or other antioxidants or mixtures thereof.

The stabilization is effective irrespective of the nature of the vitamin A derivative employed.

The active substances according to the invention may be present either as solid particles in the carrier gas or in dissolved form in the carrier gas.

For the case where the active substances are present in dissolved form in the carrier gas according to the invention two possibilities are provided, i.e. an active substance solution in a nonaqueous volatile solvent or an active substance solution in an aqueous solvent.

The solution of the active substance according to the invention may preferably be in a nonvolatile nontoxic physiologically compatible solvent.

Particularly advantageous is the use of a dosage aerosol propellent gas pack. For the production thereof the active substance is first dissolved in a toxicologically harmless inert solvent; suitable for this purpose are in particular fluorochlorohydrocarbons such as 1,1,2-trichloro-1,2,2-trifluoroethane (Frigen 13) which simultaneously also acts as a component of the propellent gas mixture. The solution is then introduced into a pressure-resistant container, for example into an aluminium can provided with an internal protective lacquer. Thereafter a propellent gas or propellent gas mixture consisting of liquefied or compressed gases, for example a mixture of low-boiling fluorochlorohydrocarbons, is introduced into the can under pressure after removal of the air from said can and the can sealed with a metering valve. The components of the propellent gas are toxicologically harmless and inert; suitable for example are dichlorodifluoromethane (Frigen 12) or 1,2-dichloro-1,1,2,2-tetrafluoromethane (Frigen 114) or liquefied gas, such as propane, butane or dimethyl ether.

Apart from this method of the socalled pressure filling according to the invention for example the refrigeration method or the "under the cup filling" method are possible.

The pharmaceutical preparation prepared according to the invention in this manner consists of:
0.01–50% by weight active substance
0–49.99% by weight solvent and
50–99.99% by weight propellent gas.

Preferably it consists of
0.01–30% by weight active substance
0–30% by weight solvent and
40–99.99% by weight propellent gas.

In particular, preparations are suitable comprising:
0.05–25% by weight active substance
0–30% by weight solvent and
45–99.95% by weight propellent gas.

Preparations are advantageous comprising:
0.1–15% by weight active substance
0–25% by weight solvent and
60 to 99.9% by weight propellent gas.

Particularly advantageous are preparations comprising
0.1–10% by weight active substance
0–25% by weight solvent and
65–99.9% by weight propellent gas.

Preparations have been found particularly advantageous which comprise:
0.1–7% by weight active substance
5–23% by weight solvent and
70–94.9% by weight propellent gas.

Also particularly advantageous is the use of preparations comprising:
0.1–5% by weight active substance
10–20% by weight solvent and
75–89.9% by weight propellent gas.

Excellent results are obtained with a preparation comprising:
0.17% by weight active substance
19.83% by weight solvent and
80% by weight propellent gas
for the administration of small individual doses of the active substance and preparations comprising
3.9% by weight active substance
20% by weight solvent and
76.1% by weight propellent gas
for administrations of large individual doses of the active substance.

The active substance contents of the last two preparations relate to retinol palmitate (1.7 million IU/g). When using other active substances or active substance mixtures the proportion in percent by weight is to be amended so that the vitamin A activity (expressed in IU) or vitamin A equivalent dosis (on a molar basis) contained in the respective amount of active substance remains unchanged. The resulting composition shifts are compensated for by appropriate modification of the percentage by weight of the solvent proportion in the preparation.

The preferred discharge amount of the metering valves employed is for example between 35 mg and 100 mg per spray shot.

Further features of the invention will be apparent from the following description of nonlimiting examples of embodiment.

EXAMPLE 1

| | |
|---|---|
| Retinol palmitate (1.7 million IU/g), stabilized with BHA/BHT | 3.9% by weight |
| 1,1,2-trichloro-1,2,2-trifluoroethane | 26.1% by weight |
| propellent gas mixture consisting of 40% by weight dichlorodifluoromethane and 60% by weight 1,2-dichloro-1,1,2,2-tetrafluoroethane | 70.0% by weight |

To prepare the active substance solution 13.0 kg retinol palmitate (1.7 million IU/g) is dissolved in 87.0 kg trichlorotrifluoroethane. The dissolving is carried out in a closed container with incorporated agitator so that no evaporation of the solvent can take place. After the dissolving the liquid is filtered through a 50 μm filter and the amount of solvent evaporated when this is done replenished. For the filling the clear active substance solution is removed from a tightly sealed container with a withdrawal conduit by means of a mechanical piston dosage device and introduced into the aerosol cans provided for this purpose. The dosage device is fixed so that it always discharges the same amount of 4.5 g per dosage stroke. Thereafter, the aerosol metering valve is fitted over the opening of the can and the valve undetachably secured (crimped) on the aerosol can using automatic crimping tongs. The can thus sealed is now filled via an automatic propellent gas filling apparatus through the valve with the respective propellent gas mixture. The filling amount for 4.5 g active substance solution is 10.5 g propellent gas. The metering valve employed is advantageously designed for a discharge of 75 mg per spray shot.

After checking the cans to ensure they are leakfree in accordance with the technical regulations for gases (TRG 402) said cans are provided with the spray head or a corresponding atomizer means which is fitted onto the valve ball of the metering valve. To protect the atomizer means from actuation and damage the can is also provided with a suitable protective cap or packed in a protective envelope.

EXAMPLE 2

| | |
|---|---|
| Retinol palmitate (1.7 million IU/g) stabilized with BHA/BHT | 0.17% by weight |
| 1,1,2-trichloro-1,2,2-trifluoroethane | 19.83% by weight |
| propellent gas mixture consisting of 40% by weight dichlorodifluoromethane and 60% by weight 1,2-dichloro-1,1,2,2-tetrafluoroethane | 80.0% by weight. |

The metering valve employed is advantageously designed for a discharge of 35 mg per spray shot.

EXAMPLE 3

| | |
|---|---|
| retinol laurate, stabilized with alpha-tocopherol | 0.14% by weight |
| propellent gas mixture consisting of 40% by weight chlorotrifluoroethylene and 60% by weight dichlorofluoromethane | 99.86% by weight |

The metering valve employed is advantageously designed for a discharge of 35 mg per spray shot.

EXAMPLE 4

| | |
|---|---|
| retinoic acid ethyl ester | 9.2% by weight |
| trichlorofluoromethane | 20.8% by weight |
| propellent gas mixture consisting of 45% by weight 1,1,-difluoroethane and 55% by weight 1,1-dichloro-1,2,2,2-tetrafluoroethane | 70% by weight |

The metering valve employed is advantageously designed for a discharge of 75 mg per spray shot.

EXAMPLE 5

Active substance mixture (stabilized with alpha-tocopherol) consisting of:

| | |
|---|---|
| retinoic acid capryl ester | 1.15% by weight |
| retinol acetate | 1.40% by weight |
| 1,1,2-trichloro-1,2,2-trifluoroethane | 22.45% by weight |
| propellent gas mixture consisting of 40% by weight 1,1-difluoroethane and 60% by weight 1,1-dichloro-1,2,2,2-tetrafuoroethane | 75.0% by weight |

The metering valve employed is advantageously designed for a discharge of 75 mg per spray shot.

EXAMPLE 6

Active substance mixture (stabilized with gamma-tocopherol) consisting of:

| | |
|---|---|
| retinol propionate | 0.05% by weight |
| retinol oleate | 0.085% by weight |
| trichlorofluoromethane | 19.865% by weight |
| propane | 80.0% by weight |

EXAMPLE 7

| | |
|---|---|
| retinol acetate, stabilized with gamma-tocopherol | 22% by weight |
| 1,1,2 trichloro-1,2,2-trifluoroethane | 22% by weight |
| propellent gas mixture consisting of 50% 1-chloro-1,1-difluoroethane and 50% tetrafluoromethane | 56% by weight |

The metering valve employed is advantageously designed for a discharge of 35 mg per spray shot.

The preparation method for examples 2 to 6 is analogous to that described under example 1. In the case of example 3 a third of the trichlorofluoromethane contained in the propellent gas mixture serves for dissolving the active substance.

The active substance mist discharged by a spray shot of the metering valve is introduced by suitable applicators into the body cavities and onto their mucous membranes. For example, it can be introduced into the mouth cavity by a mouthpiece fitted onto the spray can. From there, on inhalation after the spraying operation particles of 0.5-5 μm reach the pulmonary alveoli whilst particles of 5-30 μm are transported onto the mucous membranes of the upper respiratory tract.

Further pharmaceutical preparations according to the invention are those in which the active substances are dissolved or dispersed in aqueous solvents. These may be referred to as "aqueous systems". "Aqueous systems" is the term applied here to systems which contain as solvent water or mixtures of water with other physiologically compatible solvents.

Auxiliary substances known per se to the expert, such as emulsifiers and/or solutizers, may preferably be added to the solvent.

The active-substance-containing liquid prepared in this manner can preferably be used.

a. In the form of a three-phase liquid gas aerosol pack: the same propellent gas systems are employed as in the two-phase aerosol described above.
b. In the form of a pressurized gas aerosol: the liquid is introduced into a spray can which is subjected to pressure by means of compressed gas (e.g. nitrogen or carbon dioxide).
c. In the form of a pump aerosol.

The active substance is preferably used already stabilized with the aforementioned antioxidants. In the case of an open system, such as the pump aerosol, in which outer air gets into the container, the preparation is preferably conserved for example by addition of parabens or other suitable preservatives.

The aqueous active substance system which can be used in the manner described consists of:
0.01-50% by weight active substance
1-30% by weight emulsifier and/or solutizer
ad 100% by weight water and carrier gas.

Particularly suitable are systems comprising:
0.05-20% by weight active substance
5-30% by weight emulsifier and/or solutizer
ad 100% by weight water and carrier gas.

Advantageous is the use of systems comprising:
0.1-10% by weight active substance
5-25% by weight emulsifier and/or solutizer
ad 100% by weight water and carrier gas.

In particular systems comprising:

| |
|---|
| 0.5-5% by weight active substance |
| 10-25% by weight emulsifier and/or solutizer |
| ad 100% by weight water and carrier gas. |

A nonrestrictive example for an active system to be used according to the invention is disclosed below:

| | |
|---|---|
| retinol palmitate oily (1 million IU/g) stabilized with BHA/BHT | 1.0% by weight |
| emulsifier (Cremophor RH 40 (BASF)) | 22.0% by weight |
| 1,2-propylene glycol | 2.0% by weight |
| water and carrier gas | ad 100.0% by weight |

The pharmaceutical preparation according to the invention can advantageously be employed for preventing and treating functional impairments, diseases and pathological changes in the mucous membranes of humans and animals, in particular in the respiratory epithelium, the epithelia of the nose-throat cavity, the urogenital tract and the intestinal tract.

To the functional impairments, diseases and pathological changes which can be influenced by the invention belong in particular cellular differentiation disturbances of the mucous membranes of the respiratory tract, squamous metaplasia irrespective of the genesis, neoplastic changes, reduced activity of the ciliated epithelium, dysfunction of mucigenous cells irrespective of the genesis.

Consequently, the pharmaceutical preparations according to the invention are suitable inter alia for therapy or as adjuvant in the therapy of bronchial carcinomas, acute and chronic bronchitis, acute and chronic functional disturbances due to impairment of the tracheobronchial epithelium following inhalation of dusts and gases damaging the mucous membranes, bronchopulmonary dysplasia of newborn children and the carthagena syndrome.

The necessary daily dose lies as a rule between 100 and 50,000 IU vitamin A or vitamin A equivalent dose which subject to the toxicological acceptance as regards systemic and other side effects is administered in 1 to 10 individual doses of 100-5,000 IU vitamin A activity or vitamin A equivalent dose in corresponding intervals. However, higher individual or daily doses may be administered depending on the nature of the diseases being treated.

The invention has in particular the following advantages:

The invention ensures that the vitamin A and the other active substances according to the invention in the administration form chosen according to the invention are absorbed into the target cells.

According to the present state of the art for obtaining a remission of squamous metaplasia in humans and animals high to maximum concentrations of vitamin A must be used systemically (100,000-500,000 IU/day for up to 60 days). Hitherto, it was thus possible to show only inadequately that these squamous metaplasia not induced by vitamin A deficiency, is also quantitatively returned into the mucous-secretory original epithelium and that the metaplastically changed cell can also take up the vitamin.

The reason for this is in particular that the metaplastically changed cell no longer has at its disposal receptors for taking up the vitamin RBP complex. It was thus not to be expected that a topical intake of vitamin A without binding protein can be accepted by the cell and used for metabolic purposes in order to effect in this manner a reversibility of the squamous metaplasia.

According to the invention it was possible to show that
1. Vitamin A, for example in the form of its long-chain fatty acid esters, can be absorbed into the cells of the respiratory mucous membrane without mediation of receptors and/or binding proteins after topical administration.
2. The vitamin absorbed is converted to a metabolically activatable form.
3. The squamously metaplastically changed epithelium of the respiratory mucous membrane can be restored to its original epithelium after topical administration of the vitamin.
4. The dosages necessary for achieving adequate, i.e. effective local vitamin A concentrations in the respiratory epithelium when using an aerosol lie far below those with systemic administration.

Figure 2A:
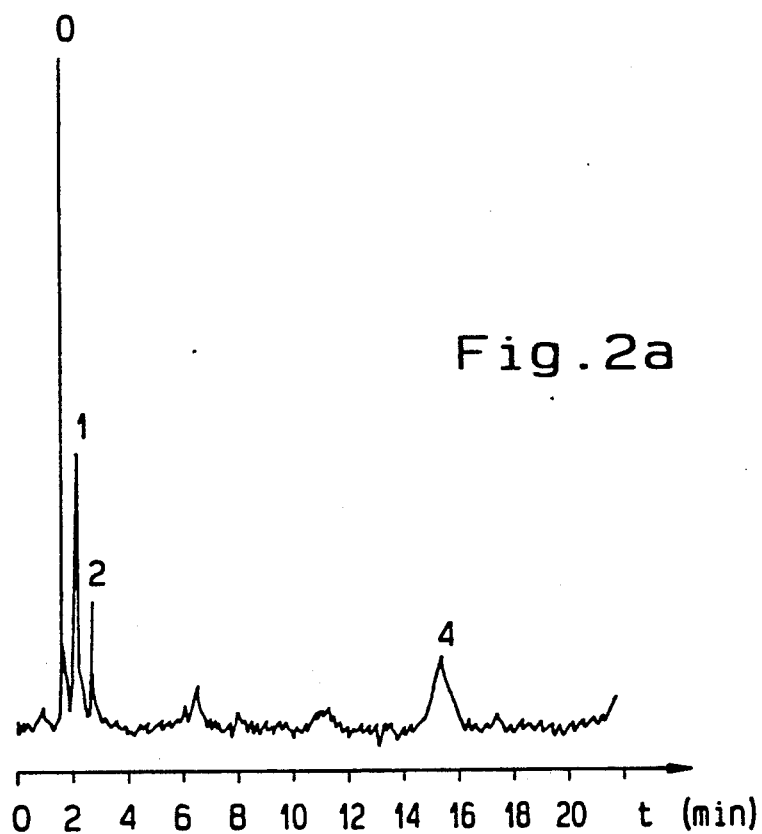
FIGS. 2a and 2b are chromatogram traces of vitamin A derivatives in accordance with the invention ten and 48 hours, respectively, after the infusion of retinyl margarinate.
Figure 2B:
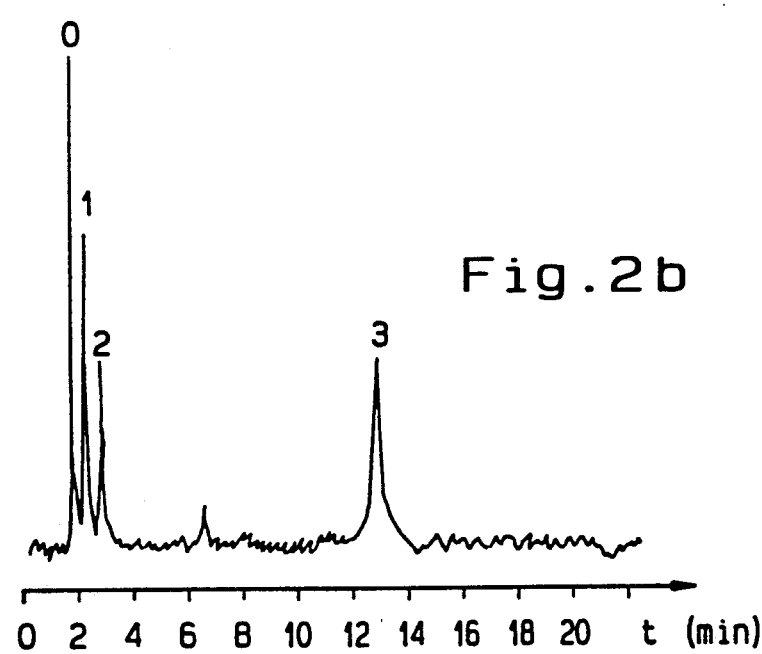

In this connection the following tests were carried out and will be explained in detail with the aid of the attached FIGS. 1, 2*a*, 2*b* and 3:

The Figures show:

FIG. 1

Distribution of retinol and retinyl esters at various times after parenteral administration of the retinyl margarinate. Vitamin A deficiency: in this case at the start of the test no derivatives of retinol were present in the tissues whilst after 48 hours an appreciable enrichment can be observed in particular in the lungs and trachea which in particular for the trachea exceeds the concentration of stored retinol esters to be measured in normal animals (rear axis).

FIGS. 2*a* and 2*b*

Chromatogramm of the investigated vitamin A derivatives 10 hours after infusion of the retinyl margarinate (2*a*) and 48 hours after infusion (2*b*).

FIG. 3

Occurrence of retinol in various target tissues of animals deprived of vitamin A 48 hours after infusion of a C 17 retinyl ester. At the start of the tests these tissues did not include any retinol so that the latter can have penetrated the tissues only by hydrolysis of the C 17 ester. In particular, no further retinol occurrence is observed in the liver and this again proves that no transesterification and separation via the liver has taken place to a quantitatively significant extent. The detection of retinol in the cells further proves that the hydrolysis of the esters has taken place in these tissues.

Remarks on the above tests:

1) Rats deprived of vitamin A in which no peripheral vitamin A stores could be detected in the respiratory epithelium were given a nonphysiological (i.e. normally not occurring but metabolizable) retinyl ester in different concentrations via an implanted infusion system for 6 hours. The kinetics were determined through continuous blood analyses so that 48 hours after the start of the test it was possible to take organ specimens to investigate the distribution of the retinyl esters in the mucous membranes of the respiratory tract but also in other tissues. It was found that the administered retinyl ester is absorbed in the mucous membrane, hydrolyzed and reverse esterified so that it is present in its metabolizable active form (FIG. 1). This therefore means that absorption of the vitamin A derivative without binding proteins is possible and the vitamin is therefore available to the target cells.

The topical administration of the C 17 retinyl ester by an atomizing method via a tracheal probe in nutritionally deficient animals led to a comparable result. The C 17 esters are absorbed in the target cells of the respiratory epithelium (FIG. 2*a*) and converted to a metabolically active form (FIG. 2*b*) as chromatographic measurements have shown.

The use of C 17 retinyl esters in animals with a nutritional vitamin A deficiency has several advantages:

Firstly, the nutritionally deficient animals do not have any vitamin A occurrences in the central and peripheral storage tissues so that a measurement of the distribution of such esters after administration is easily possible. Secondly, a C 17 retinyl ester does not naturally occur so that on detection in the target cells it can be assumed that this ester has thus been absorbed into the cell (see also FIG. 2*a*). In addition, with the aid of further retinyl esters occurring having fatty acids of different chain length hydrolysis and reverse esterification of the C 17 ester can be concluded (see also FIG. 2b).

Figure 3:
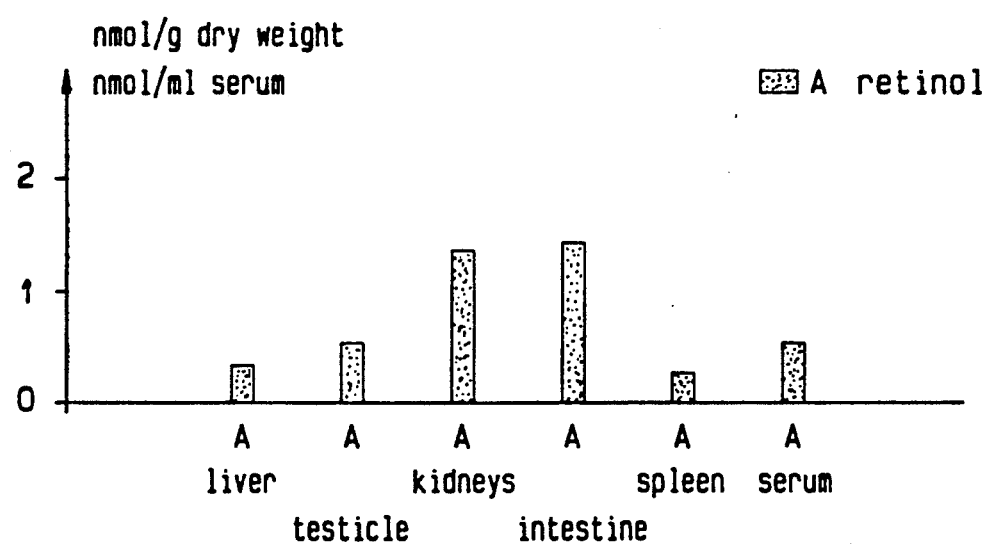
FIG. 3 is a bar graph representing the level of retinol in selected tissues of animals who were deprived of Vitamin A 48 hours after the infusion of a $C_{17}$ retinyl ester.

2) It was possible to clarify this point in the tests as described under 1). The metabolically active form of the vitamin A is retinol which after hydrolysis of the retinyl esters can develop its effect in the target cells coupled to the cellularly retinol-binding protein (CRBP). This is however possible only when the vitamin is already present in the cells as ester because the absorption of the retinol through the blood system after enteral absorption or liberation from the liver is possible only via the transport protein in the plasma (RBP). As FIG. 3 shows the topically administered C 17 retinyl ester was absorbed into the cell, esterified after hydrolysis with palmitic acid, again hydrolyzed and is then present in the cells as retinol (FIG. 3).

3) In normally fed rats by chronic inhalation of cigarette smoke condensate (CSC) a squamously metaplastic change of the tracheobronchial epithelium was induced. This metaplastic change was particularly strongly pronounced in the bronchus of the 2nd type and is distinguished by basal cell hyperplasia and focal ciliary loss. These changes were very pronounced in all the animals (n=20) treated. The systemic administration of 15,000 IU vitamin A as retinyl palmitate (2 times per week) led after on the average 22 days to a complete regression of the changes when the CSC inhalation had been stopped at the start of the vitamin A supplementation. If during the supplementation CSC inhalation was continued the changes were reversed later (on the average after 39 days) but not completely. Although the cilioneogenesis was clearly stimulated (enhanced thymidine labelling index) a few areas remained in which the basal cell hyperplasia was completely reversed, although there were still a few focal ciliary losses.

In topical administration of the vitamin by an atomizer or nebulizer via a tracheal probe with administration twice a day each of 1000 IU vitamin A as retinyl palmitate after an average of 16 days (on ceasing the CSC inhalation at the start of the topical administration) a complete remission of the squamously metaplastic changes was observed and if the CSC inhalation was continued a complete remission also occurred after 16 days.

This shows that the topical administration of retinyl esters has the great advantage over the systemic administration that even with continuous irritation of the tissue the regeneration is initiated and thus the development of neoplastic changes prevented. The decisive point is however also that far smaller concentrations were required to obtain remission and consequently systemic-toxic side effects could be avoided.

4) High enteral vitamin A administration (>25,000 IU/day) leads to a chronic hypervitaminosis A which in particular in children and pregnant women can lead to damage. Consequently, supplementation with this vitamin is therapeutically useful in human beings only in subtoxic doses of less than 25,000 IU/day. Since due to the degeneration of the membrane-bound retinol receptors the squamously metaplastically changed cell can scarcely absorb retinol from the plasma, it is dependent on the plasma retinyl esters which can reach the cell without receptors. Under normal circumstances retinyl esters occur in plasma with normal vitamin A intake only in a very low concentration so that adequate retinyl ester plasma levels are reached only on enteral supplementation of more than 100,000 IU/day. The normal concentration of on average 50 μg retinyl ester/g dry weight in the respiratory mucous membrane can be increased in rats by supplementation with at least 15,000 IU vitamin A/day to 75 μg/g. The plasma retinyl ester concentration is then about 50% of the retinyl concentration, corresponding in humans to a daily dose of 100,000 IU vitamin A. If the vitamin is applied topically to the mucous membrane (1000 IU vitamin A twice daily) the original concentration in the mucous membrane rises from 50 μg/g to 110 μg/g without an appreciable increase in the plasma retinyl ester concentration occurring. Since the toxic side effects of high enteral vitamin A intake are related to the increase in the plasma retinyl ester, the topical administration has a clear advantage of the systemic intake. Toxic side effects can be avoided in spite of longer application because firstly total concentrations for obtaining a remission are lower than with enteral intake, and an increase in the plasma retinyl esters as must be aimed at after systemic intake does not take place.

Own investigations have shown that vitamin A in the form of its retinyl esters without receptors is absorbed after topical administration by the cells of the respiratory epithelium and transferred to its metabolically active form. This result justified the investigation of the efficacy of a topical administration on the reversibility of squamous metaplasia of the respiratory epithelium. It was possible to show that in the case of chronic vitamin A depletion by topical administration of the aerosol a. the absorption into the squamously metaplastically changed cells takes place, b. the squamously metaplastically changed cells are restored to their original phenotype, c. to obtain this restoration in the topical administration subtoxic, i.e. physiological, concentrations were sufficient whilst with systemic administration only the large-dosage administration was successful.

By using a vitamin A-containing aerosol squamous metaplasia as occur due to acute and chronic bronchitis, vitamin A deficiency or due to inhaled carcinogenic substances or physical and chemical irritations, can be restored to their original phenotype. The aerosol employed has the advantage that physiological can be employed and a systemic effect, in particular of toxic nature, can be avoided.

Advantageously the invention can be applied in particular for treating metaplasia of the cells of the mucous membranes of the respiratory tract, in particular the squamous epithelium.

What is claimed is:

1. An aerosol-inhalate pharmaceutical preparation comprising 0.01–50% by weight of at least one active substance selected from the group consisting of an ester of retinol and an ester of retinoic acid, and, in the case of dust aerosols, the balance of the composition 50–99.99% by weight carrier gas, and in the case of mist aerosols, the balance of the composition selected from the group consisting of:

(a) 0–49.99% by weight non-aqueous lipophilic readily volatile and physiologically compatible solvent, and 50–99.99% by weight propellant gas; and (b) 50–99.99% by weight water or water plus a water-miscible, physiologically compatible liquid and carrier gas.

2. A pharmaceutical preparation according to claim 2 in which said active substance is a member selected form the group consisting of esters of retinol with physiologically compatible carboxylic acids and esters of retinoic acid with alcohols.

3. A pharmaceutical preparation according to claim 2 in which said active substance is selected from the group consisting of retinol esters of saturated and unsaturated fatty acids.

4. A pharmaceutical preparation according to claim 1 in which said fatty acids are selected from the group consisting of palmitic acid, stearic acid, oleic acid, linoleic acid and linolenic acid.

5. A pharmaceutical preparation according to claim 2 in which said active substance is a retinoic acid ester prepared from an alcohol which is either monovalent or multivalent; primary, secondary or tertiary; and aliphatic alicyclic or aromatic.

6. A pharmaceutical preparation according to claim 2 in which said active substance is a retinoic acid ester prepared from an aliphatic, monovalent, primary alcohol.

7. A pharmaceutical preparation according to claim 2 in which said active substance is a retinoic acid ester prepared from a member selected from the group consisting of methanol, ethanol, and fatty alcohols.

8. A pharmaceutical preparation according to claim 1 in which said active substance is present as solid particles in the carrier gas.

9. A pharmaceutical preparation according to claim 1 in which active substance is present in the form of an active-substance-containing liquid in the carrier gas.

10. A pharmaceutical preparation according to claim 1 in which said active substance is dispersed in the carrier gas comprised of a propellant gas or propellant gas mixture.

11. A pharmaceutical preparation according to claim 1 in which said active substance is dissolved in said non-aqueous lipophilic readily volatile and physiologically compatible solvent.

12. A pharmaceutical preparation according to claim 1 in which said active substance is dissolved in said carrier gas selected from the group consisting of a liquified propellant gas or propellant gas mixture.

13. A pharmaceutical preparation according to claim 1 in which said active substance is dissolved in said solvent selected from the group consisting of 1,1,2-trichloro-1,2,2-trifluoroethane or trichlorofluoromethane.

14. A pharmaceutical preparation according to claim 1 in which said aerosol-inhalate is a dust aerosol and said active substance is dispersed in said carrier gas selected from the group consisting of low-boiling fluorohydrocarbons, low-boiling fluorochlorohydrocarbons, and liquified compounds which are gaseous at room temperature and atmospheric pressure.

15. A pharmaceutical preparation according to claim 1 in which said aerosol-inhalate is a dust aerosol and said active substance is dispersed in said carrier gas selected from the group consisting of dichlorodifluoromethane, 1,2-dichloro-1,1,2,2-tetrafluoroethane, 1,2-dichloro-1,2,2,2-tetrafluoroethane, chlorotrifluoroethalene, dichlorofluoromethane, 1,1-difluoroethane, 1-chloro-1,1-difluoroethane, tetrafluoromethane, mixtures thereof, liquified propane, liquified butane, and liquified dimethylether.

16. A pharmaceutical preparation according to claim 1 in which said aerosol-inhalate is a dust aerosol and said active substance is dispersed in said carrier gas selected from the group consisting of compressed nitrogen, compressed carbon dioxide, compressed dinitrogenoxide, and compressed air.

17. An aerosol-inhalate pharmaceutical preparation comprising 0.01% to 50% by weight of at least one active substance selected from the group consisting of an ester of retinol and an ester of retinoic acid, the aerosol-inhalate in the form of a mist aerosol, said preparation further comprising 0% to 49.99% by weight of a non-aqueous lipophilic readily volatile and physiologically compatible solvent and 50% to 99.99% by weight of a propellant gas.

18. An aerosol-inhalate pharmaceutical preparation comprising 0.01% to 30% by weight of at least one active substance selected from the group consisting of an ester of retinol and an ester of retinoic acid, the aerosol-inhalate being a mist aerosol, said preparation further comprising 0% to 30% by weight of a non-aqueous lipophilic readily volatile and physiologically compatible solvent, and 40% to 99.99% by weight of a propellant gas.

19. An aerosol-inhalate pharmaceutical preparation comprising 0.05% to 25% by weight of at least one active substance selected from the group consisting of an ester of retinol and an ester of retinoic acid, said aerosol-inhalate in the form of a mist aerosol, said preparation further comprising 0% to 30% by weight of a non-aqueous lipophilic readily volatile and physiologically compatible solvent, and 45% to 99.99% by weight of a propellant gas.

20. An aerosol-inhalate pharmaceutical preparation comprising 0.1% to 15% by weight of at least one active substance selected from the group consisting of an ester of retinol and an ester of retinoic acid, the aerosol-inhalate in the form of a mist aerosol, said preparation further comprising 0% to 25% by weight of a non-aqueous lipophilic readily volatile and physiologically compatible solvent and 60% to 99.99% by weight of a propellant gas.

21. An aerosol-inhalate pharmaceutical preparation comprising 0.1% to 10% by weight of at least one active substance selected from the group consisting of an ester of retinol and an ester of retinoic acid, said aerosol-inhalate in the form of a mist aerosol, said preparation further comprising 0% to 25% by weight of a non-aqueous lipophilic readily volatile and physiologically compatible solvent, and 65% to 99.99% by weight of a propellant gas.

22. An aerosol-inhalate pharmaceutical preparation comprising 0.1% to 7% by weight of at least one active substance selected from the group consisting of an ester of retinol and an ester of retinoic acid, said aerosol-inhalate in the form of a mist aerosol, said preparation further comprising 5% to 23% by weight of a non-aqueous lipophilic readily volatile and physiologically compatible solvent, and 70% to 94.9% by weight of a propellant gas.

23. An aerosol-inhalate pharmaceutical preparation comprising 0.1% to 5% by weight of at least one active substance selected from the group consisting of an ester of retinol and an ester of retinoic acid, said aerosol-inhalate in the form of a mist aerosol, said preparation further comprising 10% to 20% by weight of a non-aqueous lipophilic readily volatile and physiologically compatible solvent, and 75% to 89.9% by weight of a propellant gas.

24. An aerosol-inhalate pharmaceutical preparation comprising 0.17% by weight retinol palmitate, said preparation in the form of a mist-aerosol, said preparation further comprising 19.83% by weight of a non-aqueous lipophilic readily volatile and physiologically compatible solvent, and 80% by weight of a propellant gas.

25. An aerosol-inhalate pharmaceutical preparation comprising 3.9% by weight retinol palmitate, said aerosol-inhalate in the form of a mist-aerosol, said preparation further comprising 20 by weight of a non-aqueous lipophilic readily volatile and physiologically compatible solvent, and 76.1% by weight of a propellant gas.

26. An aerosol-inhalate pharmaceutical preparation comprising 0.01% to 50% by weight of at least one active substance selected from the group consisting of an ester of retinol and an ester of retinoic acid, said aerosol-inhalate in the form of a mist-aerosol, said preparation further comprising 1% to 30% by weight of an emulsifier and/or water-miscible, physiologically compatible liquid, the balance comprised of water and carrier gas.

27. An aerosol-inhalate pharmaceutical preparation comprising 0.05% to 20% by weight of at least one active substance selected from the group consisting of an ester of retinol and an ester of retinoic acid, said aerosol-inhalate in the form of a mist-aerosol, said preparation further comprising 5% to 30% by weight of an emulsifier and/or water-miscible, physiologically compatible solvent, the balance comprised of water and carrier gas.

28. An aerosol-inhalate pharmaceutical preparation comprising 0.01% to 10% by weight of at least one active substance selected from the group consisting of an ester of retinol and an ester of retinoic acid, said aerosol-inhalate in the form of a mist-aerosol, said preparation further comprising 5% to 25% by weight of an emulsifier and/or water-miscible, physiologically compatible liquid, the balance comprised of water and carrier gas.

29. An aerosol-inhalate pharmaceutical preparation comprising 0.05% to 5% by weight of at least one active substance selected from the group consisting of an ester of retinol and an ester of retinoic acid, said aerosol-inhalate in the form of a mist-aerosol, said preparation further comprising 10% to 25% by weight of an emulsifier and/or water-miscible, physiologically compatible liquid, the balance comprised of water and carrier gas.

30. An aerosol-inhalate pharmaceutical preparation comprising retinol palmitate oil (1 million Iu/g) at 1.0% by weight stabilized with BHA/BHT, said preparation further comprising 22.0% by weight of an emulsifier, 2.0% by weight 1,2-propylene glycol, the balance comprised of water and carrier gas.

* * * * *